US012588950B2

(12) United States Patent
Zagorchev

(10) Patent No.: US 12,588,950 B2
(45) Date of Patent: Mar. 31, 2026

(54) TRAJECTORY PLANNING FOR MINIMALLY INVASIVE THERAPY DELIVERY USING LOCAL MESH GEOMETRY

(71) Applicant: ClearPoint Neuro, Inc., Solana Beach, CA (US)

(72) Inventor: Lyubomir Zagorchev, Burlington, MA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 257 days.

(21) Appl. No.: 18/327,420

(22) Filed: Jun. 1, 2023

(65) Prior Publication Data

US 2023/0389989 A1     Dec. 7, 2023

Related U.S. Application Data

(60) Provisional application No. 63/348,359, filed on Jun. 2, 2022.

(51) Int. Cl.
*A61B 34/10* (2016.01)
*G16H 20/40* (2018.01)
*G16H 50/50* (2018.01)
(52) U.S. Cl.
CPC ............. *A61B 34/10* (2016.02); *G16H 20/40* (2018.01); *G16H 50/50* (2018.01); *A61B 2034/105* (2016.02); *A61B 2034/107* (2016.02)

(58) Field of Classification Search
CPC .............. A61B 34/10; A61B 2034/105; A61B 2034/107; G16H 20/40; G16H 50/50; G16H 30/20; G16H 30/40
See application file for complete search history.

(56) References Cited

U.S. PATENT DOCUMENTS

| | | | | |
|---|---|---|---|---|
| 2017/0065349 A1* | 3/2017 | Ourselin | ................ | A61B 34/10 |
| 2018/0199848 A1* | 7/2018 | Wendling | ............... | A61B 5/374 |
| 2019/0105105 A1* | 4/2019 | Zagorchev | ............. | G09B 23/30 |
| 2022/0287686 A1* | 9/2022 | Kruecker | ................ | A61B 8/14 |
| 2023/0124879 A1* | 4/2023 | Krishnan | ................. | G06T 7/30 |
| | | | | 382/128 |

OTHER PUBLICATIONS

Li et al. 2019 Neurotherapeutics 16:182â191 (Year: 2019).*
Wenzel et al. 2018 Medical Image Analysis 46:146â161 (Year: 2018).*

* cited by examiner

*Primary Examiner* — Keith M Raymond
*Assistant Examiner* — Patrick M Mehl
(74) *Attorney, Agent, or Firm* — Sheppard Mullin Richter & Hampton LLP

(57) ABSTRACT

Systems and methods are provided for determining surgical trajectories (including target points and entry points) for delivering therapy to a patient's brain using a three-dimensional (3D) representation of the patient's brain (including the patient's scalp, skull, and brain) adapted from imaging data (e.g., MRI data, CT data, etc.) of the patient's brain.

20 Claims, 10 Drawing Sheets

302

302

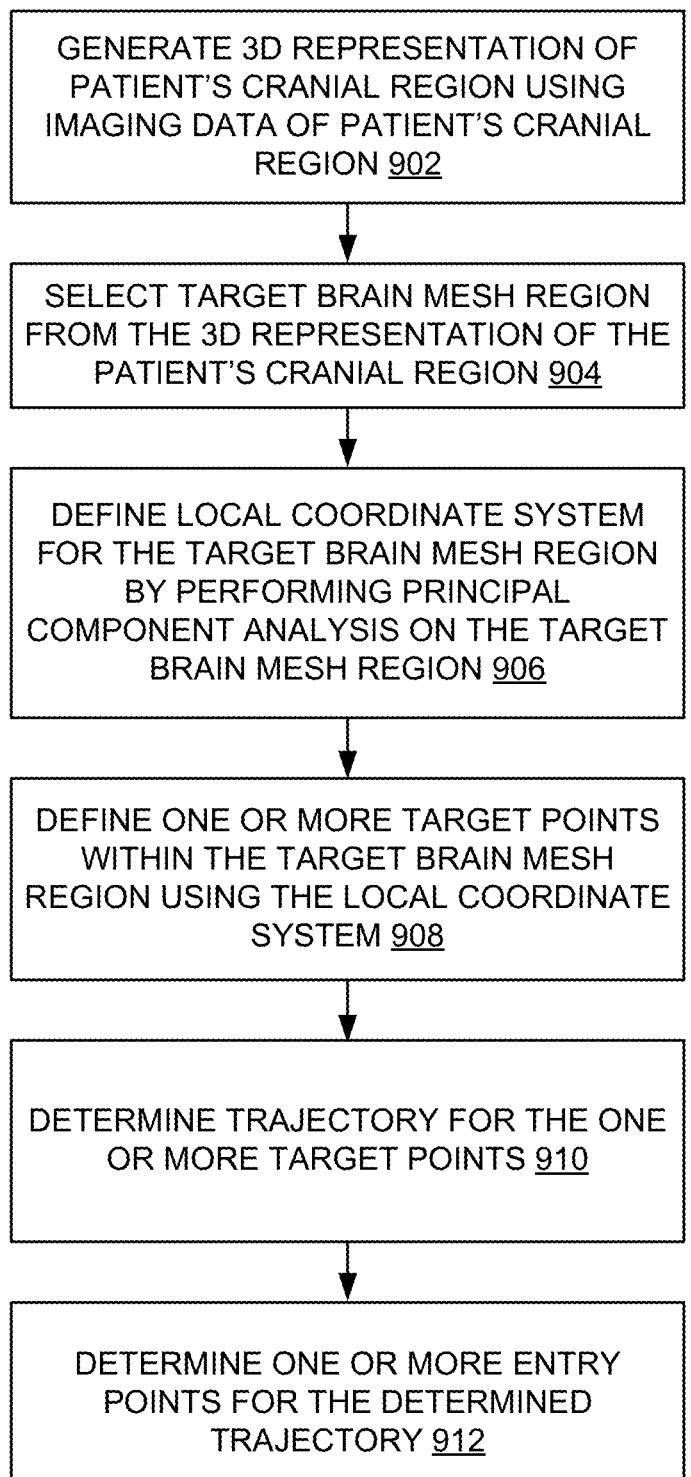

GENERATE 3D REPRESENTATION OF PATIENT'S CRANIAL REGION USING IMAGING DATA OF PATIENT'S CRANIAL REGION 902

SELECT TARGET BRAIN MESH REGION FROM THE 3D REPRESENTATION OF THE PATIENT'S CRANIAL REGION 904

DEFINE LOCAL COORDINATE SYSTEM FOR THE TARGET BRAIN MESH REGION BY PERFORMING PRINCIPAL COMPONENT ANALYSIS ON THE TARGET BRAIN MESH REGION 906

DEFINE ONE OR MORE TARGET POINTS WITHIN THE TARGET BRAIN MESH REGION USING THE LOCAL COORDINATE SYSTEM 908

DETERMINE TRAJECTORY FOR THE ONE OR MORE TARGET POINTS 910

DETERMINE ONE OR MORE ENTRY POINTS FOR THE DETERMINED TRAJECTORY 912

FIG. 9

TRAJECTORY PLANNING FOR MINIMALLY INVASIVE THERAPY DELIVERY USING LOCAL MESH GEOMETRY

RELATED APPLICATIONS

This application claims the benefit of and priority to U.S. Provisional Patent Application No. 63/348,359, filed on Jun. 2, 2022, the contents of which are incorporated herein by reference in their entirety.

TECHNICAL FIELD

The present disclosure relates generally to medical technologies, and more particularly, some examples relate to trajectory planning for minimally invasive therapy delivery using local mesh geometries.

BRIEF DESCRIPTION OF THE DRAWINGS

The present disclosure, in accordance with one or more various examples, is described in detail with reference to the following figures. The figures are provided for purposes of illustration only and merely depict examples.

FIG. 9 depicts an example flow diagram that may be performed by examples of the presently disclosed technology to determine a trajectory for delivering therapy to a region of interest of a patient's brain, in accordance with various examples of the presently disclosed technology.

Figure 1:
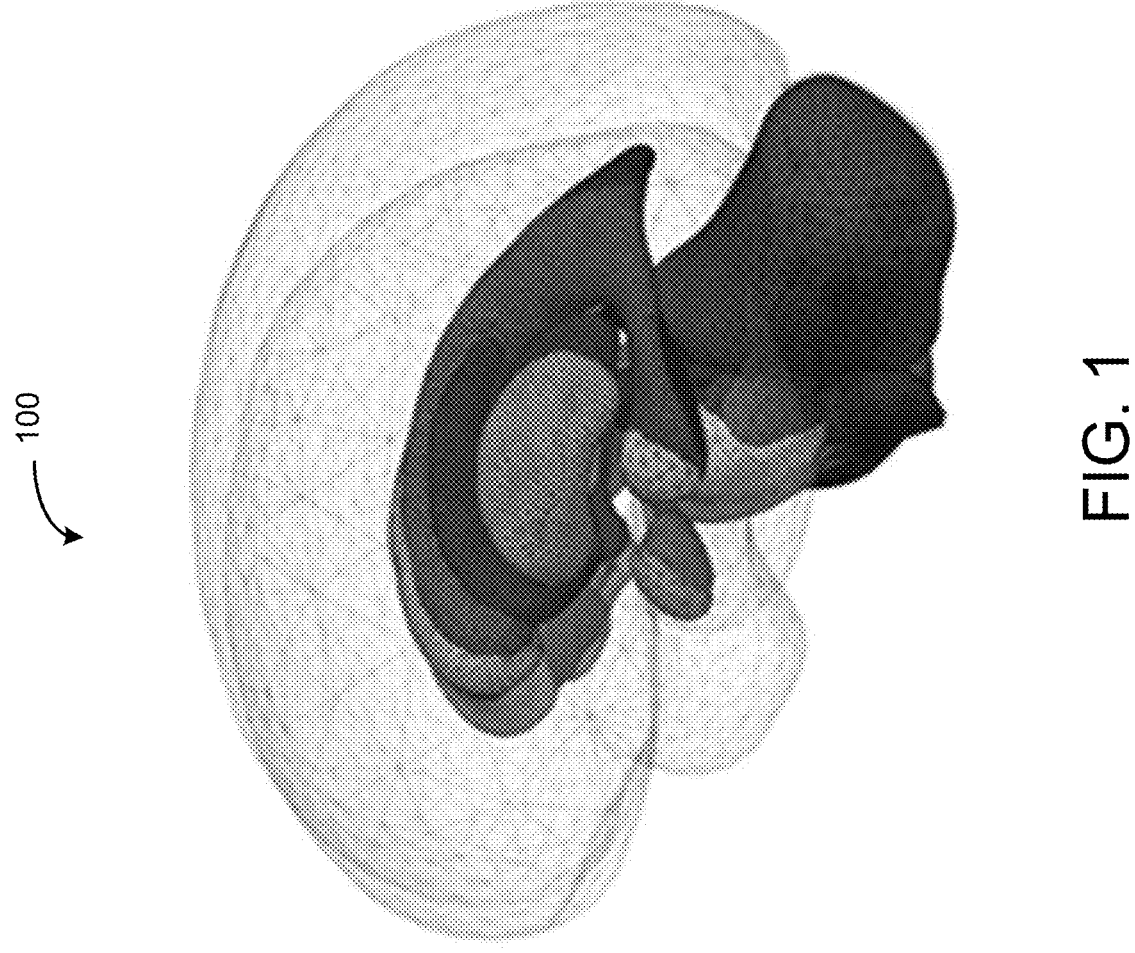
FIG. 1 depicts an example mean shape representation of a shape-constrained deformable brain model, in accordance with various examples of the presently disclosed technology.

The figures are not exhaustive and do not limit the present disclosure to the precise form disclosed.

DETAILED DESCRIPTION

Various therapies (e.g., drug therapies, laser therapies, deep brain stimulation, etc.) can treat genetic and acquired brain diseases, but their delivery can be a significant challenge. An advantage of minimally invasive brain interventions is that they can deliver therapy to targeted brain regions directly while minimizing the size of incisions made in a patient's cranial region (i.e., brain, skull, scalp, etc.). To achieve safe and effective delivery, such interventions require careful planning of (1) target point(s) within a targeted region of the patient's brain for delivering therapy; (2) entry point(s) for entering the patient's scalp/skull/brain; and (3) trajectories for reaching the target point(s) from the entry point(s). Variability introduced in the planning process can adversely affect the efficacy of delivered therapy and should be avoided. Carefully planned and reproducible trajectories can achieve better outcomes at typically lower doses. They can also simplify clinical workflows and make therapy delivery safer and more predictable across different patient and clinical sites.

Against this backdrop, examples of the presently disclosed technology provide systems and methods for planning/determining trajectories for delivering therapy to a targeted region of a patient's brain using a three-dimensional (3D) representation of the patient's brain (including the patient's scalp, skull, and brain) adapted from imaging data (e.g., MRI data, CT data, etc.) of the patient's brain. Such planning may also comprise determining entry points for entering the patients skull and/or scalp in order to achieve the planned trajectory.

The patient-specific 3D representation of a patient's brain, which may be referred to as a patient-specific shape-constrained deformable brain model, may comprise a mesh. As used herein a mesh may refer to a representation of a larger domain (e.g., a volume or surface) comprised of smaller discrete cells called mesh elements (e.g., mesh triangles or other shapes), and mesh vertices at the junctions of adjoining mesh elements. Meshes can be used to compute solutions to equations across individual mesh elements, which then can be used to approximate solutions over the larger domain.

Within the patient-specific shape-constrained deformable brain model, a given mesh element may represent a given region of the patient's brain, skull, or scalp. As will be described in greater detail below, examples may utilize meshes to compute/derive a local coordinate system fora target brain region (in particular examples may perform principal component analysis on mesh vertices of a target brain mesh region to derive a local coordinate system for the target brain mesh region/target brain region). Examples may then leverage this derived local coordinate system to determine improved/optimal trajectories for therapy delivery to the target brain region.

As alluded to above, the patient-specific shape-constrained deformable brain model may be generated by adapting a generalized model (i.e., a mean shape representation of the shape-constrained deformable brain model) to imaging data of a patient's brain (e.g., MRI scans, CT scans, etc., which may be referred to herein as head scans). By adapting a generalized/mean shape representation to patient-specific imaging data commonly obtained in clinical settings, examples of the presently disclosed technology can be easily reproduced across different patients/subjects, physicians, sites, etc. Accordingly, examples of the presently disclosed technology may improve upon existing trajectory planning technologies (e.g., visual target point selection using multi-modal fusion) which are more time consuming and not as easily reproducible across different patients/subjects, physicians, sites, etc.

After adaptation of the patient-specific shape-constrained deformable brain model to a patient-specific scan, examples may select a target brain mesh region from the larger model.

This target brain mesh region may represent a region of the patient's brain that has been targeted (by e.g., a surgeon or clinician) for therapy delivery. Like the patient-specific shape-constrained deformable brain model, the target brain mesh region may be a mesh comprising mesh elements and mesh vertices.

After the target brain mesh region has been selected, examples may perform principal component analysis (PCA) on mesh vertices of the target brain mesh region (as used herein, PCA may refer to a process for transforming data into a new coordinate system). Examples may then utilize eigen vectors and eigen values derived from the PCA to define a local coordinate system for the target brain mesh region. As alluded to above, examples may leverage this local coordinate system for the target brain mesh region/ target brain region to determine improved/optimal trajectories for delivering therapy to the target brain region.

The local coordinate system may define the long axis of the target brain mesh region (as used herein a long axis may refer to an axis/line extending through the center of an object in a lengthwise direction). In certain instances, the local coordinate system may also define a short axis orthogonal to the long axis. In some cases, examples of the presently disclosed technology may also estimate modes of variation for the target brain mesh region based on the PCA performed. Examples may utilize these modes of variation for automatic trajectory selection.

Utilizing the PCA-derived local coordinate system for the target brain mesh region, examples may define one or more target points within the target brain mesh region. These target points/coordinates can be encoded in the PCA-derived local coordinate system. Encoding target points in the local coordinate system can be advantageous because such encoding makes the target points invariant of any geometric transformations (e.g. rotation, translation, etc.) applied to the image/imaging data (e.g., an MRI scan) that the patient-specific shape-constrained deformable brain model is derived from (in various examples these transformations may occur in the Digital Imaging and Communications in Medicine (DICOM) space). Additionally, if different local coordinate systems are derived using PCA of the same target brain mesh region in different patients/subjects, target points encoded in those local coordinate systems can be visualized/ compared without additional geometric transformations regardless of image/imaging data orientation.

Examples of the presently disclosed technology can select target points in various ways. For instance, examples may select target points at equal distance along the long axis, target points with pre-defined spacing from each other, etc. Examples may utilize these target points to determine trajectories for reaching the target brain mesh region.

Where two or more target points are defined within the target brain mesh region, examples may utilize various techniques for determining a trajectory and/or entry point(s) for reaching the two or more target points. For instance, examples may determine a trajectory for two or more target points by fitting a regression line (e.g., a least squares regression line) to the two or more target points. By extending this trajectory/regression line to mesh boundary surfaces (of the patient-specific shape-constrained deformable brain model) representing the patient's skull and/or scalp, examples may determine entry point(s) for the determined trajectory using line-mesh intersection in 3D.

Where only a single target point is defined within the target brain mesh region, examples may determine a trajectory using a direction vector originating at the defined target point. Examples may compute the direction vector in various ways. For instance, examples may compute the direction vector by subtracting a selected target point from (a) a prospective entry point, (b) another point of interest in the target brain mesh region, or (c) any other point of interest extracted from the patient-specific shape-constrained deformable brain model. Examples may also determine the direction vector in response to user input (e.g., where a user provides a prospective entry point).

In some cases, examples may utilize deviation between a given direction vector and the long axis of the target brain mesh region to e.g., limit the potential pool of direction vectors, or to quantify how optimal the given direction vector is with respect to the long axis.

As discussed above, where an entry point has not been defined for the determined trajectory, examples may determine an entry point for the determined trajectory by extending the direction vector to mesh boundary surfaces (of the patient-specific shape-constrained deformable brain model) representing the patient's skull and/or scalp. Examples may then determine entry point(s) for the determined trajectory using line-mesh intersection in 3D.

In various examples, utilizing the local coordinate system defined above, examples may define sub-regions within the target brain mesh region (i.e., target brain mesh sub-regions). Similar to the target brain mesh region, each target brain mesh sub-region may represent a sub-region of the region of the brain targeted for therapy delivery. In various examples, these target brain mesh sub-regions may be oriented along the long axis of the target brain mesh region.

Splitting target brain mesh region into sub-regions can facilitate improved therapy delivery. For example, if a given therapy has to cover a large brain structure, that cannot be accomplished with a single deposit. Accordingly, examples may define multiple target points across multiple target brain mesh sub-regions to ensure improved therapy coverage with multiple deposits. In addition, examples may utilize the mesh geometry within a given target brain mesh sub-region to estimate optimal target points within the given target brain mesh sub-region.

Examples may utilize various criteria for defining target brain mesh sub-regions such as: (1) length along the long axis, (2) brain mesh sub-regions having equal volume, (3) brain mesh sub-regions having particular surface curvatures; etc. As discussed above, for a given therapy, it may be advantageous/necessary to deliver the given therapy at multiple deposit locations within the targeted brain region for therapy delivery. Examples of the presently disclosed technology may take this factor into account when defining target brain mesh sub-regions. In other words, in accordance with prescriptions/requirements of a given therapy, examples may improve/optimize therapy deliver through intelligent definition of target brain mesh sub-regions. By defining at least one target point within each target brain mesh sub-region, examples may determine a trajectory for therapy delivery which reaches each target brain mesh sub-region. Accordingly, therapy may be delivered within each target brain mesh sub-region along the trajectory.

FIG. 1 depicts an example mean shape representation 100 for a shape-constrained deformable brain model, in accordance with various examples of the presently disclosed technology.

As alluded to above, mean shape representation 100 may be a generalized model which can be adapted to multiple patients using imaging data (e.g., MRI scans, CT scans, etc.) of the patients' brain.

As depicted, mean shape representation 100 is comprised of mesh elements and mesh vertices at the junctions of adjoining/adjacent mesh elements. As described above, a mesh may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. For instance, as will be described in conjunction with FIG. 4, examples may perform principal component analysis (PCA) on mesh vertices of a target brain mesh region in order to derive a local coordinate system for a target brain region represented by the target brain mesh region. Examples may then use this PCA-derived local coordinate system to determine improved/optimal trajectories for therapy delivery to the target brain region.

As described above, each mesh element of mean shape representation 100 may represent a different brain region. In the specific example of FIG. 1, the mesh elements of mean shape representation 100 comprise triangles, but in other examples mesh elements may comprise different shapes.

As described above, mean shape representation 100 can be transformed into a patient-specific representation by adapting mean shape representation 100 to imaging data (e.g., MRI data, CT data, etc.) of a particular patient's brain. Such an adaptation preserves point-based correspondences between vertices of mean shape representation 100 and the patient-specific representation's shape after adaptation to patient-specific data. Such preservation can be used to establish point-based correspondences for target brain regions for therapy delivery across varied populations. As alluded to above, this aspect of the presently disclosed technology facilitates accurate and easily reproducible trajectory planning across varied patients, physicians, sites, etc. By adapting a generalized/mean shape representation to patient-specific imaging data commonly obtained in clinical settings, examples of the presently disclosed technology can be easily reproduced across different patients/subjects, physicians, sites, etc. Accordingly, examples of the presently disclosed technology may improve upon existing trajectory planning technologies (e.g., visual target point selection using multi-modal fusion) which are more time consuming and not as easily reproducible across different patients/subjects, physicians, sites, etc.

Figure 2:
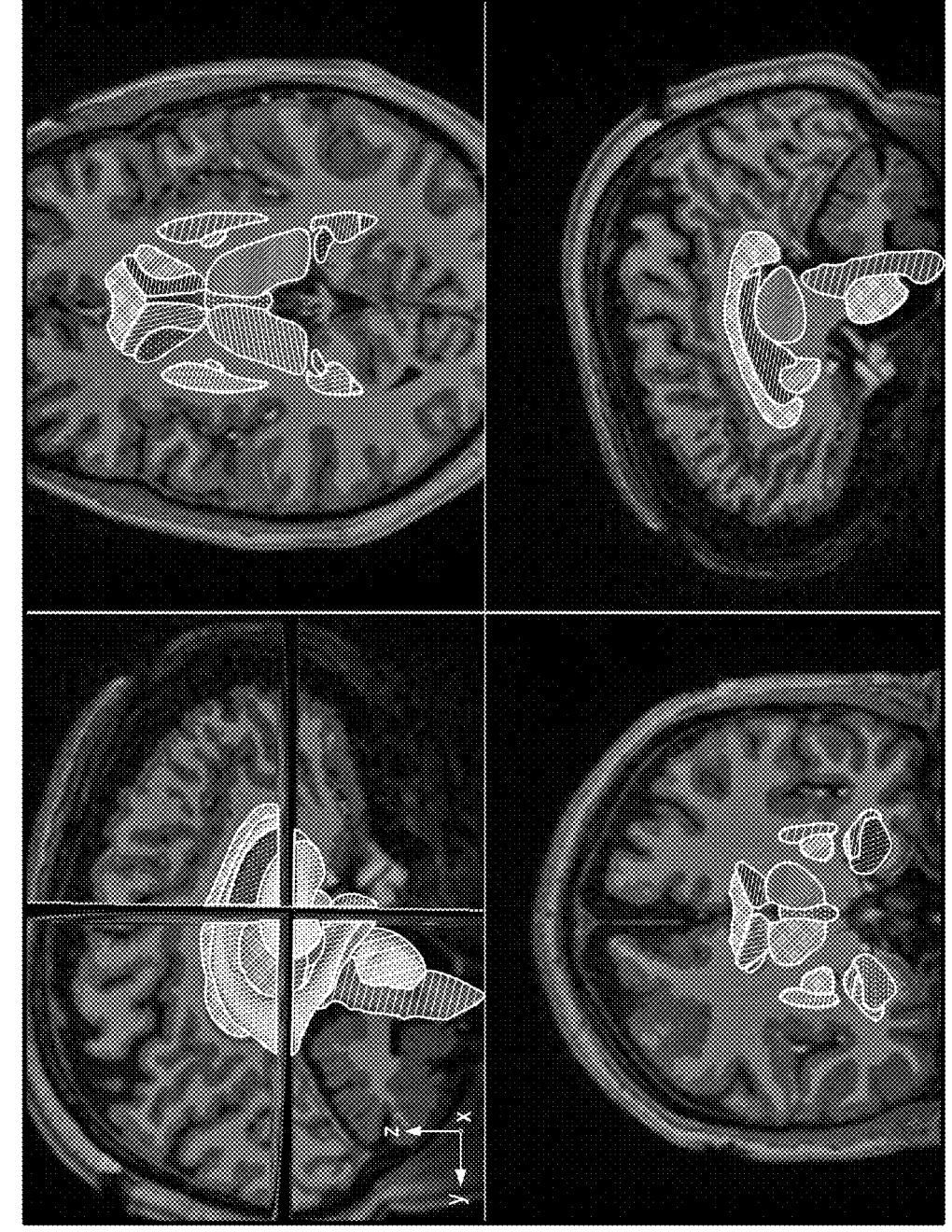
FIG. 2 depicts perspective views of an example patient-specific shape-constrained deformable brain model, in accordance with various examples of the presently disclosed technology.

FIG. 2 depicts four perspective views of an example patient-specific shape-constrained deformable brain model 200, in accordance with various examples of the presently disclosed technology. In various examples, patient-specific shape-constrained deformable brain model 200 may be the product of adapting mean shape representation 100 to imaging data of a specific patient's brain. As depicted, patient-specific shape-constrained deformable brain model 200 comprises a 3D representation of a patient's brain, including the patient's brain, skull, and scalp.

Figure 3:
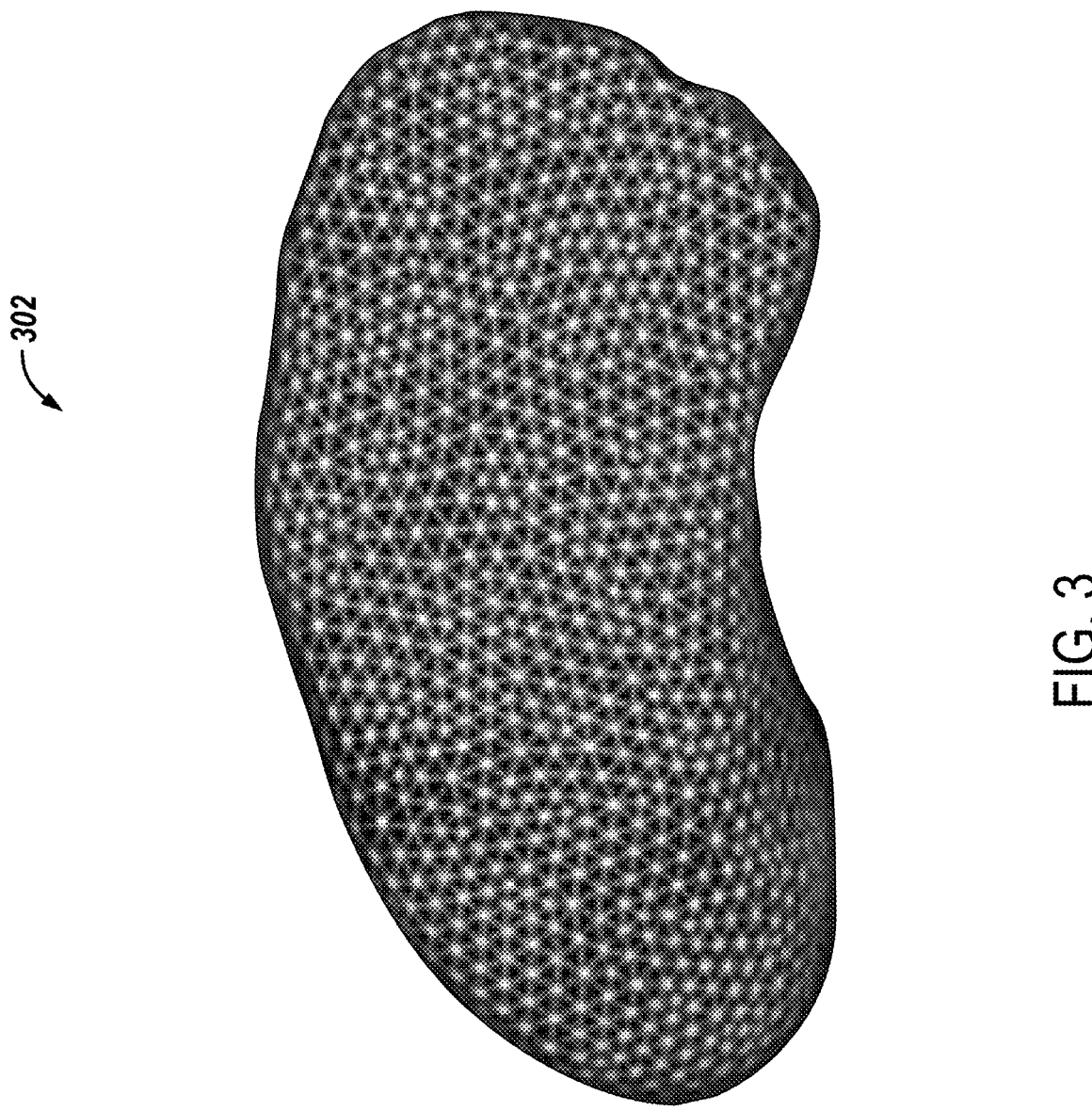
FIG. 3 depicts an example target brain mesh region, in accordance with various examples of the presently disclosed technology.

FIG. 3 depicts an example target brain mesh region 302, in accordance with various examples of the presently disclosed technology. In various examples, target brain mesh region 302 may be a target brain mesh region selected from patient-specific shape-constrained deformable brain model 200.

As described above, target brain mesh region 302 may correspond to a targeted region/volume of the patient's brain for delivering therapy (as determined by e.g., a surgeon or clinician). In the specific example of FIG. 3, target brain mesh region 302 represents a patient's putamen. However in other examples target brain mesh region 302 may represent other regions/volumes or structures of a patient's brain.

Similar to mean shape representation 100 and patient-specific shape-constrained deformable brain model 200, target brain mesh region 302 may be comprised of mesh elements and mesh vertices (in the specific example of FIG. 3, the mesh elements are mesh triangles). As will be described in conjunction with FIG. 4, examples may perform principal component analysis (PCA) on the mesh vertices of target brain mesh region 302 in order to define a local coordinate system for target brain mesh region 302.

Figure 4:
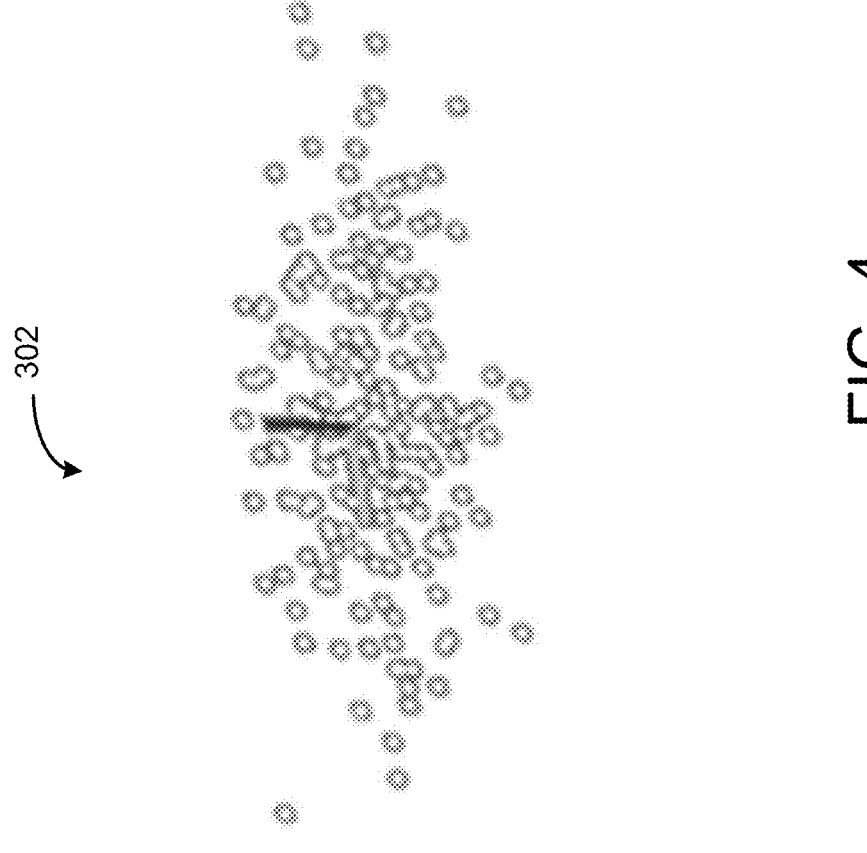
FIG. 4 depicts an example of principal component analysis being performed on a target brain mesh region, in accordance with various examples of the presently disclosed technology.

FIG. 4 depicts an example of PCA being performed on the mesh vertices of target brain mesh region 302, in accordance with various examples of the presently disclosed technology.

As depicted in FIG. 4, the mesh vertices of target brain mesh region 302 are represented as points in 3D space. Examples may utilize PCA to calculate the principal components of target brain mesh region 302 using a covariance matrix of mesh vertices. The calculated principal components represent the modes of variation for target brain mesh region 302, or how target brain mesh region 302 varies in space. Accordingly, examples may define a local coordinate target brain mesh region 302 utilizing PCA by, e.g., utilizing the three most dominant modes of variation for target brain mesh region 302, the first 3 eigen vectors of the covariance matrix of mesh vertices, etc.

Figure 5:
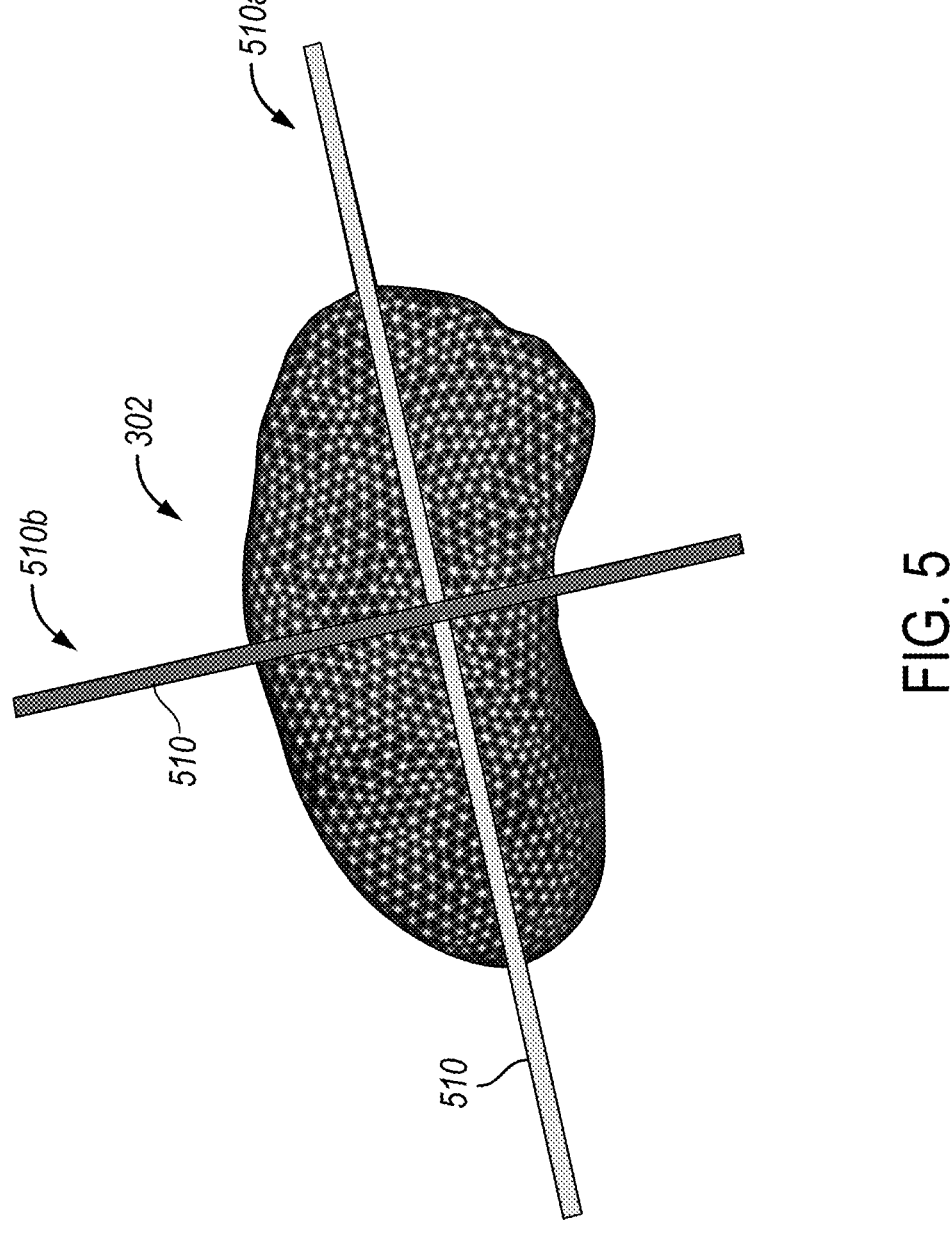
FIG. 5 depicts an example local coordinate system for a target brain mesh region, in accordance with various examples of the presently disclosed technology

FIG. 5 depicts an example local coordinate system 510 for target brain mesh region 302, in accordance with various examples of the presently disclosed technology.

As depicted, local coordinate system 510 may be oriented along a long axis (i.e. long axis 510a). Long axis 510a may be an axis of local coordinate system 510 which extends through the center of target brain mesh region 302 lengthwise.

As depicted, local coordinate system 510 may also comprise a short axis 510b that is orthogonal to long axis 510a.

As described above (and to be described below), examples may utilize local coordinate system 510 to (1) define target points within target brain mesh region 302; and (2) determine/calculate trajectories for reaching the defined target points.

Figure 6:
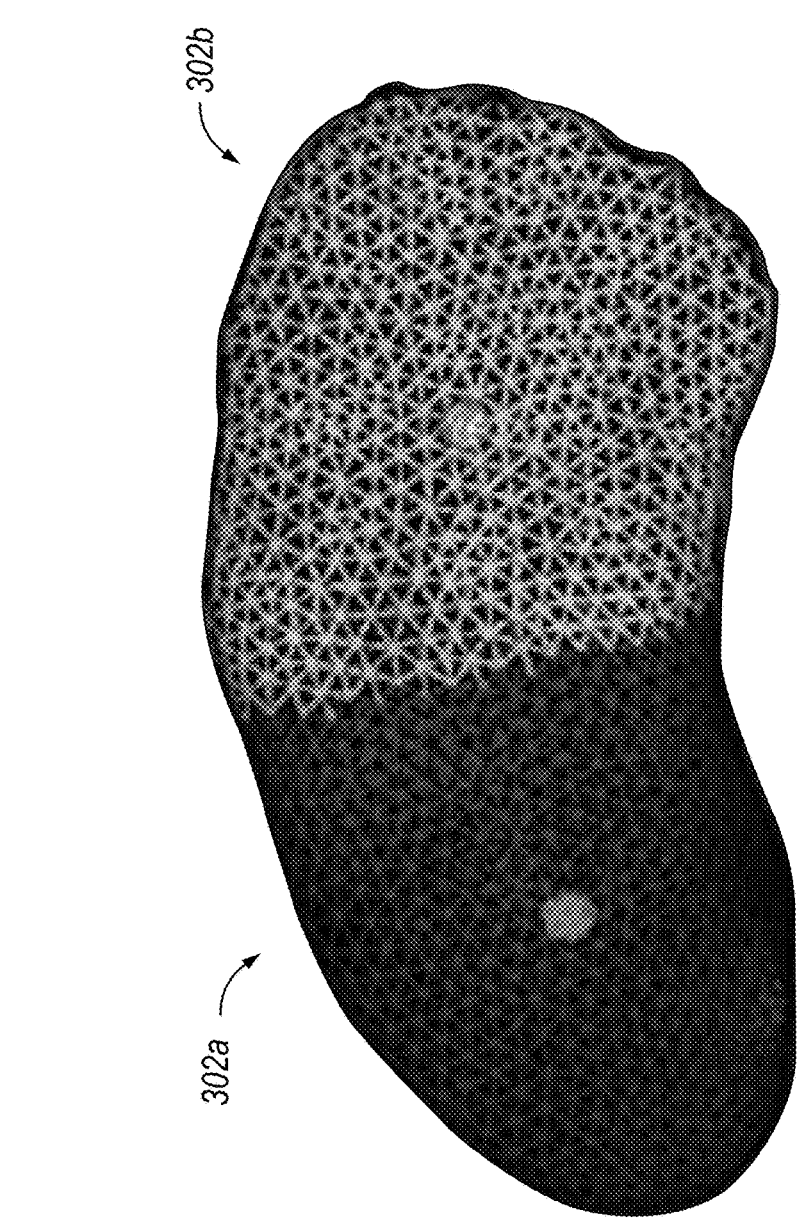
FIG. 6 depicts example target brain mesh region split into two sub-regions, in accordance with various examples of the presently disclosed technology.

FIG. 6 depicts example target brain mesh region 302 split into two sub-regions (i.e., target brain mesh subregions 302a and 302b), in accordance with various examples of the presently disclosed technology.

As described above, in certain instances, examples of the presently disclosed technology may define sub-regions with a target brain mesh region. Each target brain mesh sub-region may represent a sub-region of the region of the patient's brain targeted for delivering therapy.

Examples may utilize various criteria for defining target brain mesh sub-regions such as: (1) length along the long axis for the target brain mesh region, (2) brain mesh sub-regions having equal volume, (3) brain mesh sub-regions having particular surface curvatures; etc. As depicted in FIG. 6, target brain mesh subregions 302a and 302b represent sub-regions of target brain mesh region 302 having equal distances along long axis 510a of local coordinate system 510.

As described above, splitting a target brain mesh region into sub-regions can facilitate improved therapy delivery. For example, if a given therapy has to cover a large brain structure, that cannot be accomplished with a single deposit. Accordingly, examples may define multiple target points across multiple target brain mesh sub-regions to ensure improved therapy coverage with multiple deposits. In addition, examples may utilize the mesh geometry within a given target brain mesh sub-region to estimate optimal target points within the given target brain mesh sub-region.

Figure 7:
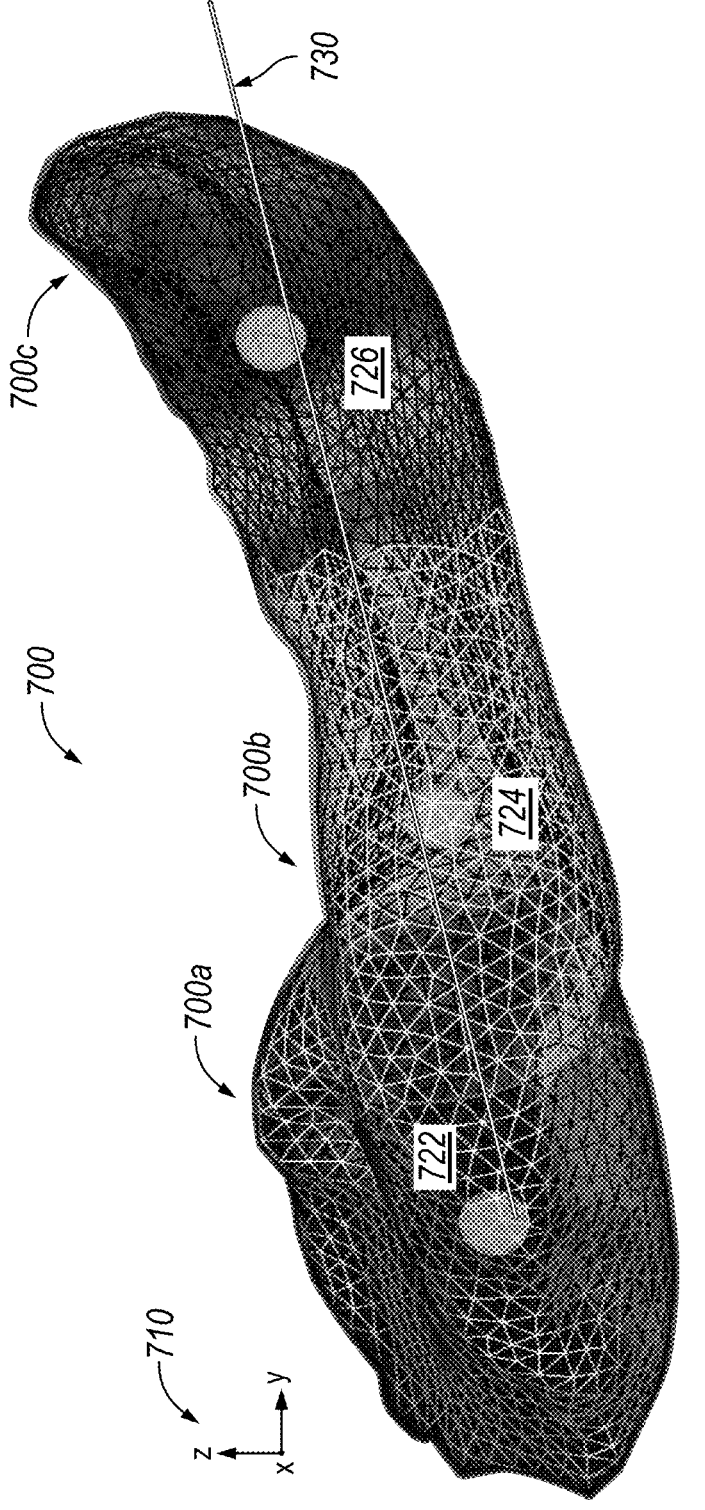
FIG. 7 depicts another example target brain mesh region, in accordance with various examples of the presently disclosed technology.

FIG. 7 depicts an example target brain mesh region 700, in accordance with various examples of the presently disclosed technology. In various examples target brain mesh region 700 may be another target brain mesh region selected from patient-specific shape-constrained deformable brain model 200. Like target brain mesh region 302, target brain mesh region 700 is comprised of mesh elements and mesh vertices. Similarly, examples may have performed PCA on the mesh vertices of target brain mesh region 700 in order to define a local coordinate system 710 for target brain mesh region 700. Local coordinate system 710 may comprise a long axis (not pictured) extending through the center of target brain mesh region 700 lengthwise.

As described above, examples may define sub-regions for target brain mesh region 700. As depicted in the example of FIG. 7, three sub-regions have been defined for target brain mesh region 700: target brain mesh sub-region 700a; target brain mesh sub-region 700b; and target brain mesh sub-region 700c. Target brain mesh sub-regions 700a-c may be oriented along the long axis for local coordinate system 710. In particular, target brain mesh sub-regions 700a-c may be defined such that they each have an equal distance along the long axis for local coordinate system 710.

As described above, depending on a given therapy, it may be advantageous/necessary to deliver the given therapy at multiple locations and/or sub-regions within the brain region targeted for therapy. Examples of the presently disclosed technology may take this factor into account when defining target brain mesh sub-regions 700a-c. In other words, in accordance with prescriptions/requirements of a given therapy, examples may improve/optimize therapy deliver through intelligent definition of target brain mesh sub-regions. By defining at least one target point within each target brain mesh sub-region, examples may determine a trajectory for therapy delivery which reaches each target brain mesh sub-region. Accordingly, therapy may be delivered within each target brain mesh sub-region along the trajectory.

Thus, in the example of FIG. 7, a target point has been defined in each of target brain mesh sub regions 700a-c (i.e. target points 722, 724, and 726). As described above, examples may define target points 722-726 using local coordinate system 710. Examples may utilize target points 722-726 to determine trajectories for reaching target brain mesh region 700, and more particularly, each of target brain mesh sub regions 700a-c.

As described above, examples may utilize various techniques for determining a trajectory and entry point(s) for reaching target points 722-726. For instance, examples may determine a trajectory for target points 722-726 by fitting a regression line (e.g., a least squares regression line) to target points 722-726. An example regression line 730 for target points 722-726 is depicted in FIG. 7. By extending regression line 730 to mesh boundary surfaces representing the patient's skull and/or scalp, examples may determine entry point(s) for the determined trajectory using techniques such as line-mesh intersection in 3D. The mesh boundary surfaces representing the patients skull and scalp may be mesh boundary surfaces of the patient-specific shape-constrained deformable brain model from which target brain mesh region 700 has been selected, and may represent both interior and exterior surfaces of the patient's skull and scalp.

Figure 8:
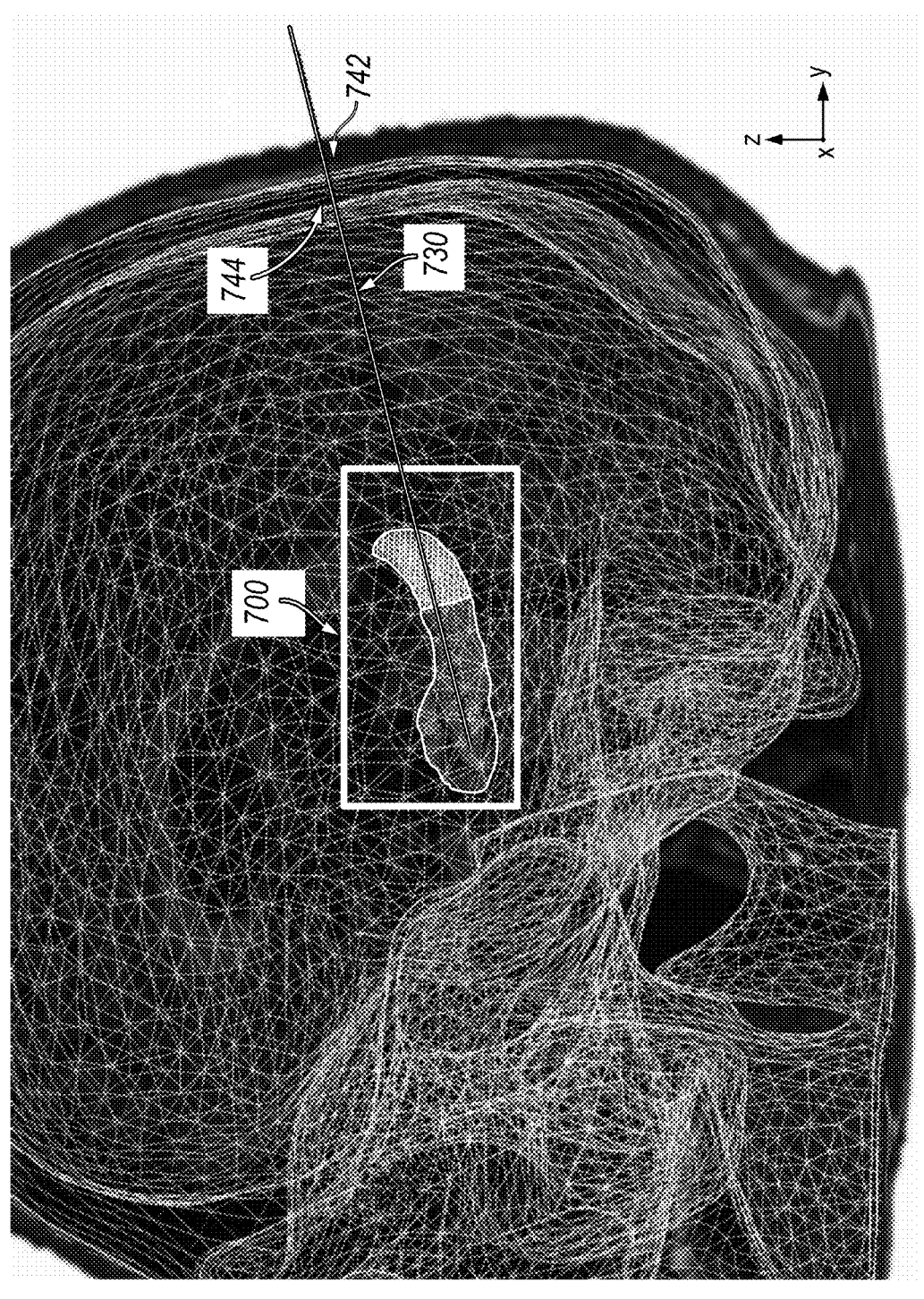
FIG. 8 depicts an example of how a planned/determined trajectory may be extended to mesh boundary surfaces representing a patient's skull and scalp in order to determine entry points for the trajectory.

FIG. 8 depicts how regression line 730 may be extended to mesh boundary surfaces representing the patient's skull and scalp. Using techniques such as line-mesh intersection in 3D, examples may then define entry points at the patients skull, scalp, and/or brain (e.g., entry points 740, 742, and 744) for the trajectory represented by regression line 730.

FIG. 9 depicts an example flow diagram that may be used to determine a trajectory for delivering therapy to a targeted region of a patient's brain, in accordance with various examples of the presently disclosed technology.

At operation 902, examples may generate a 3D representation of the patient's brain using imaging data of the patient's brain. As described in the preceding figures, examples may utilize a mean shape representation of a shape-constrained deformable brain model as a basis for this operation. The mean shape representation of the shape-constrained deformable brain model may comprise a 3D representation of a generalized human brain that can be adapted for use with multiple patients. As described above, this mean shape representation of the shape-constrained deformable brain model may be a mesh comprising mesh elements and mesh vertices at the junctions of adjoining/adjacent mesh elements. The mesh may consists of sub-meshes where each sub-mesh may represent a different anatomical brain structure within the brain.

As described above, examples may generate the 3D representation of the patient's brain by adapting the mean shape representation of the shape-constrained deformable brain model to imaging data (e.g., MRI data, CT data, etc.) of the patient's brain. In this way, the 3D representation of the patient's brain generated at operation 902 may be specifically adapted/tailored to the patient.

Like the mean shape representation of the shape-constrained deformable brain model, the 3D representation of the patient's brain may be a mesh comprising mesh elements and mesh vertices at the junctions of adjoining/adjacent mesh elements. Each mesh element may represent a region of the patient's brain (i.e., brain, skull, scalp, etc.).

At operation 904, examples may select a target brain mesh region (e.g., a sub-mesh) from the 3D representation of the patient's brain. As described above, this target brain mesh region may correspond to/represent a region of the patient's brain targeted for delivering therapy. Like the 3D representation of the patient's brain, the target brain mesh region may be comprised of mesh elements and mesh vertices.

At operation 906, examples may define a local coordinate system for the target brain mesh region by performing principal component analysis (PCA) on the mesh vertices of the target brain mesh region. In particular, examples may utilize eigen vectors and eigen values derived from the PCA to define the local coordinate system for the target brain mesh region. In some examples, the local coordinate system may be oriented along the long axis of the target brain mesh region (as used herein a long axis may refer to an axis/line extending through the center of an object lengthwise). In some cases, examples of the presently disclosed technology may estimate modes of variation for the target brain mesh region based on the PCA performed.

At operation 908, examples may define one or more target points within the target brain mesh region using the local coordinate system. As described above, the one or more target points may be used to determine trajectories for delivering therapy to the targeted region of the patient's brain represented by the target brain mesh region.

At operation 910, examples may determine a trajectory for the one or more target points defined at operation 908.

As described above, where two or more target points are defined within the target brain mesh region, examples may utilize various techniques for determining a trajectory for the two or more target points. For example, examples may determine a trajectory for two or more target points by fitting a regression line (e.g., a least squares regression line) to the two or more target points. Where only a single target point is defined within the target brain mesh region, examples may determine a trajectory using a direction vector originating at the defined target point.

As described above, in some cases, examples may define sub-regions within the target brain mesh region (i.e., target brain mesh subregions) utilizing the local coordinate system defined at operation 906. Similar to the target brain mesh region, each target brain mesh sub-region may represent a sub-region of the brain region of interest for delivering therapy. In various examples, these target brain mesh sub-regions may be oriented along the long axis of the target brain mesh region.

Examples may utilize various criteria for defining target brain mesh sub-regions such as: (1) length along the long axis, (2) brain mesh sub-regions having equal volume, (3) brain mesh sub-regions having particular surface curvatures; etc. Depending on a given therapy, it may be advantageous/ necessary to deliver the given therapy at multiple locations and/or sub-regions within the brain region of interest for therapy. Examples of the presently disclosed technology may take this factor into account when defining target brain mesh sub-regions. In other words, in accordance with pre-scriptions/requirements of a given therapy, examples may improve/optimize therapy delivery through intelligent defi-nition of target brain mesh sub-regions. By defining at least one target point within each target brain mesh sub-region, examples may determine a trajectory for therapy delivery which reaches each target brain mesh sub-region. Accord-ingly, therapy may be delivered within each target brain mesh sub-region along the trajectory.

At operation 912, examples may determine one or more entry points for the trajectory determined at operation 910.

As described above, where the determined trajectory is represented by a regression line fit to two or more target points, examples may determine entry points by extending the regression line to mesh boundary surfaces representing the patient's skull and/or scalp (these mesh boundary sur-faces of the skull and scalp may be mesh boundary surfaces of the 3D representation of the patient's brain). Accordingly, examples may determine entry point(s) at the patient's skull and/or scalp surfaces for the determined trajectory using line-mesh intersection in 3D (here, the entry point may be defined using a global coordinate system of an image (of the patient's brain) in DICOM space, but can be transformed to the local coordinate system; such a transformation can be advantageous as it makes the entry point independent of geometric transformations applied to the image). Where a determined trajectory is represented by a direction vector originating at a single target point, examples may determine entry points in the same/similar manner by extending the direction vector to mesh boundary surfaces representing the patient's skull and/or scalp, and using line-mesh intersection in 3D to determine entry points at the patient's skull and/or scalp.

Figure 10:
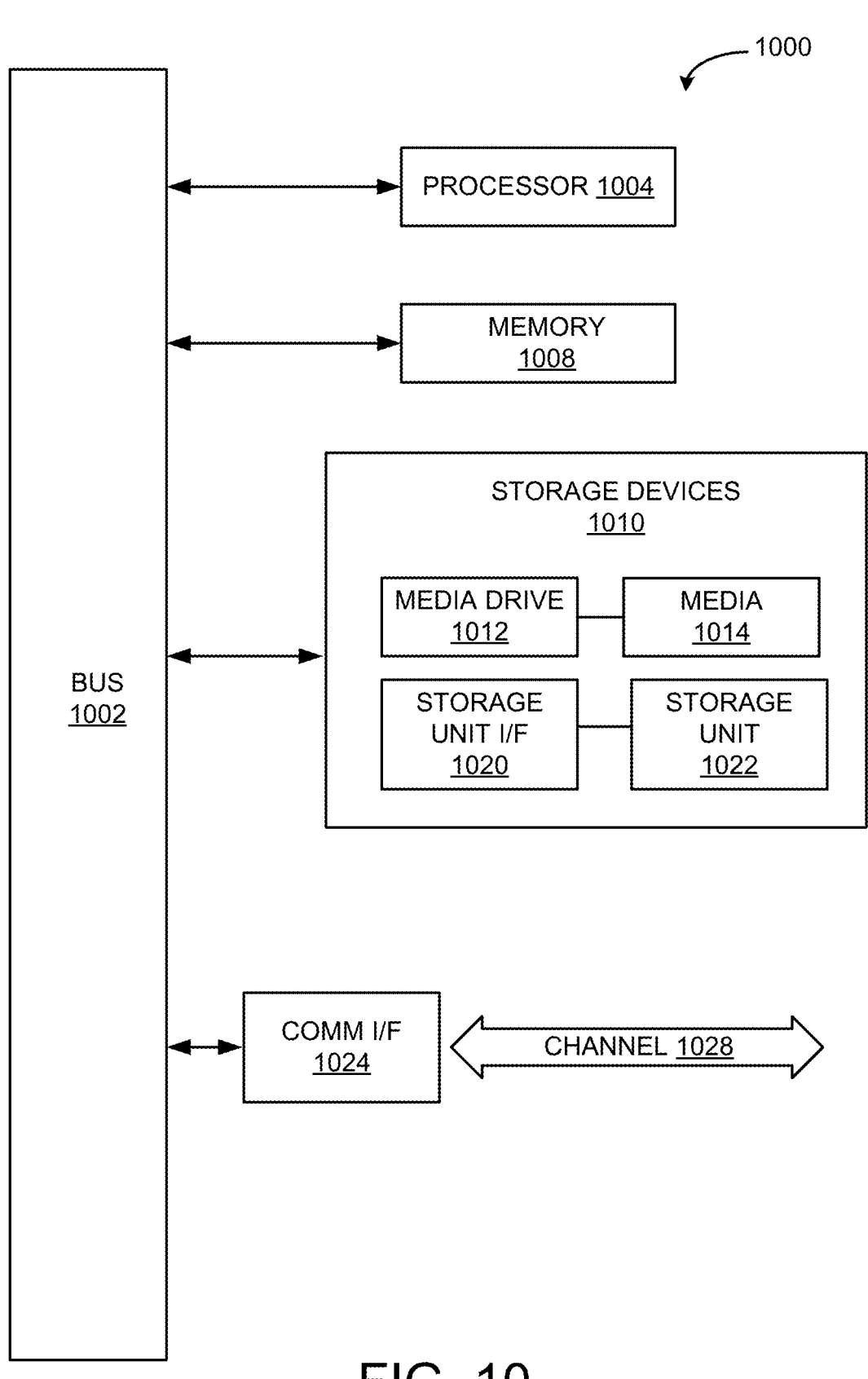
FIG. 10 is an example computing component that may be used to implement various features of examples described in the present disclosure.

As used herein, the terms circuit and component might describe a given unit of functionality that can be performed in accordance with one or more examples of the present application. As used herein, a component might be imple-mented utilizing any form of hardware, software, or a combination thereof. For example, one or more processors, controllers, ASICs, PLAs, PALs, CPLDs, FPGAs, logical components, software routines or other mechanisms might be implemented to make up a component. Various compo-nents described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional ele-ments may be individually described or claimed as separate components, it should be understood that these features/ functionality can be shared among one or more common software and hardware elements. Such a description shall not require or imply that separate hardware or software components are used to implement such features or func-tionality.

Where components are implemented in whole or in part using software, these software elements can be implemented to operate with a computing or processing component capable of carrying out the functionality described with respect thereto. One such example computing component is shown in FIG. 10. Various examples are described in terms of this example-computing component 1000. After reading this description, it will become apparent to a person skilled in the relevant art how to implement the application using other computing components or architectures.

Referring now to FIG. 10, computing component 1000 may represent, for example, computing or processing capa-bilities found within a self-adjusting display, desktop, lap-top, notebook, and tablet computers. They may be found in hand-held computing devices (tablets, PDA's, smart phones, cell phones, palmtops, etc.). They may be found in work-stations or other devices with displays, servers, or any other type of special-purpose or general-purpose computing devices as may be desirable or appropriate for a given application or environment. Computing component 1000 might also represent computing capabilities embedded within or otherwise available to a given device. For example, a computing component might be found in other electronic devices such as, for example, portable computing devices, and other electronic devices that might include some form of processing capability.

Computing component 1000 might include, for example, one or more processing resources, such as, but not limited to, processors, controllers, control components, or other pro-cessing devices. Processor 1004 might be implemented using a general-purpose or special-purpose processing engine such as, for example, a microprocessor, controller, or other control logic. Processor 1004 may be connected to a bus 1002. However, any communication medium can be used to facilitate interaction with other components of computing component 1000 or to communicate externally.

Computing component 1000 might also include one or more memory components, simply referred to herein as main memory 1008. For example, random access memory (RAM) or other dynamic memory, might be used for storing information and instructions to be executed by processor 1004. Main memory 1008 might also be used for storing temporary variables or other intermediate information dur-ing execution of instructions to be executed by processor 1004. Computing component 1000 might likewise include a read only memory ("ROM") or other static storage device coupled to bus 1002 for storing static information and instructions for processor 1004.

The computing component 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a solid-state drive, a magnetic tape drive, an optical drive, a compact disc (CD) or digital video disc (DVD) drive (R or RW), or other removable or fixed media drive might be provided. Storage media 1014 might include, for example, a hard disk, an integrated circuit assembly, magnetic tape, cartridge, optical disk, a CD or DVD. Storage media 1014 may be any other fixed or removable medium that is read by, written to or accessed by media drive 1012. As these examples illustrate, the storage media 1014 can include a computer usable storage medium having stored therein computer software or data.

In alternative examples, information storage mechanism 1010 might include other similar instrumentalities for allowing computer programs or other instructions or data to be loaded into computing component 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory component) and memory slot. Other examples may include a PCMCIA slot and card, and other fixed or removable storage units 1022 and interfaces 1020 that allow software and data to be transferred from storage unit 1022 to computing component 1000.

Computing component 1000 might also include a communications interface 1024. Communications interface 1024 might be used to allow software and data to be transferred between computing component 1000 and external devices. Examples of communications interface 1024 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 1024 may be carried on signals, which can be electronic, electromagnetic (which includes optical) or other signals capable of being exchanged by a given communications interface 1024. These signals might be provided to communications interface 1024 via a channel 1028. Channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory computer-readable media. Such media may be, e.g., memory 1008, storage unit 1022, media 1014, and channel 1028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 1000 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

What is claimed is:

1. A method, comprising:

adapting a shape-constrained deformable brain model to a head scan of a patient to generate a patient-specific 3D mesh representation of the patient's brain;

selecting a target 3D mesh brain region from the patient-specific 3D mesh representation of the patient's brain;

defining a local coordinate system for the target 3D mesh brain region by performing principal component analysis (PCA) on mesh vertices of the target 3D mesh brain region;

defining 3D mesh sub-regions for the target 3D mesh brain region utilizing the local coordinate system such that at least one of:

the 3D mesh sub-regions have substantially equal length along a long axis of the target 3D mesh brain region, or the 3D mesh sub-regions have substantially equal volume;

defining one or more target points within each 3D mesh sub-region of the target 3D mesh brain region using the local coordinate system;

determining a trajectory for the target points;

determining one or more entry points for the trajectory;

generating a graphical representation of the trajectory and the one or more entry points; and displaying, on a graphical user interface (GUI), the graphical representation of the trajectory and the one or more entry points.

2. The method of claim 1, wherein defining the local coordinate system for the target 3D mesh brain region comprises:

deriving eigen vectors and eigen values from the PCA to define the local coordinate system for the target 3D mesh brain mesh region.

3. The method of claim 1, wherein the local coordinate system is oriented along the long axis of the target 3D mesh brain mesh region.

4. The method of claim 1, wherein the trajectory for the target points is determined using a direction vector originating at the target points.

5. The method of claim 4, wherein determining the one or more entry points for the trajectory comprises:

extending the direction vector to mesh boundary surfaces representing one of the patient's skull and the patient's scalp; and using line-mesh intersection in 3D to determine the one or more entry points at the one of the patient's skull and the patient's scalp.

6. The method of claim 1, wherein defining the one or more target points within each 3D mesh sub-region of the target 3D mesh brain region using the local coordinate system comprises:

fitting a regression line to the target points.

7. The method of claim 6, wherein determining the one or more entry points for the trajectory comprises:

extending the regression line to mesh boundary surfaces representing one of the patient's skull and the patient's scalp; and using line-mesh intersection in 3D to determine the one or more entry points at the one of the patient's skull and the patient's scalp.

8. The method of claim 1, wherein the head scan comprises image data of the patient's brain.

9. The method of claim 1, wherein displaying the graphical representation of the trajectory and the one or more entry points comprises at least one of:

displaying the graphical representation of the trajectory and the one or more entry points relative to the patient-specific 3D mesh representation of the patient's brain; or displaying the graphical representation of the trajectory and the one or more entry points overlaid on the head scan of the patient.

10. The method of claim 1, wherein:

the target 3D mesh brain region represents a subcortical structure; and the 3D mesh sub-regions represent sub-regions of the subcortical structure.

11. A system comprising:

a graphical user interface (GUI);

one or more processing resources; and non-transitory computer-readable memory, coupled to the one or more processing resources, having stored therein instructions that when executed by the one or more processing resources cause the system to perform a method comprising:

adapting a shape-constrained deformable brain model to a head scan of a patient to generate a patient-specific 3D mesh representation of the patient's brain;

selecting a target 3D mesh brain region from the patient-specific 3D mesh representation of the patient's brain;

defining a local coordinate system for the target 3D mesh brain region by performing principal component analysis (PCA) on mesh vertices of the target 3D mesh brain region;

defining 3D mesh sub-regions for the target 3D mesh brain region utilizing the local coordinate system such that at least one of:

the 3D mesh sub-regions have substantially equal length along a long axis of the target 3D mesh brain region, or the 3D mesh sub-regions have substantially equal volume;

defining one or more target points within each 3D mesh sub-region of the target 3D mesh brain region using the local coordinate system;

determining a trajectory for the target points;

determining one or more entry points for the trajectory;

generating a graphical representation of the trajectory and the one or more entry points; and displaying, on the GUI, the graphical representation of the trajectory and the one or more entry points.

12. The system of claim 11, wherein defining the local coordinate system for the target 3D mesh brain region comprises:

deriving eigen vectors and eigen values from the PCA to define the local coordinate system for the target 3D mesh brain mesh region.

13. The system of claim 11, wherein the local coordinate system is oriented along the long axis of the target 3D mesh brain mesh region.

14. The system of claim 11, wherein the trajectory for the target points is determined using a direction vector originating at the target points.

15. The system of claim 14, wherein determining the one or more entry points for the trajectory comprises:

extending the direction vector to mesh boundary surfaces representing one of the patient's skull and the patient's scalp; and using line-mesh intersection in 3D to determine the one or more entry points at the one of the patient's skull and the patient's scalp.

16. The system of claim 11, wherein defining the one or more target points within each 3D mesh sub-region of the target 3D mesh brain region using the local coordinate system comprises:

fitting a regression line to the target points.

17. The system of claim 16, wherein determining the one or more entry points for the trajectory comprises:

extending the regression line to mesh boundary surfaces representing one of the patient's skull and the patient's scalp; and using line-mesh intersection in 3D to determine the one or more entry points at the one of the patient's skull and the patient's scalp.

18. The system of claim 11, wherein displaying the graphical representation of the trajectory and the one or more entry points comprises at least one of:

displaying the graphical representation of the trajectory and the one or more entry points relative to the patient-specific 3D mesh representation of the patient's brain; or displaying the graphical representation of the trajectory and the one or more entry points overlaid on the head scan of the patient.

19. The system of claim 11, wherein:

the target 3D mesh brain region represents a subcortical structure; and the 3D mesh sub-regions represent sub-regions of the subcortical structure.

20. A non-transitory computer-readable storage medium including instructions that, when executed by at least one processor of a computing system, cause the computing system to perform a method comprising:

adapting a shape-constrained deformable brain model to a head scan of a patient's brain to generate a patient-specific 3D mesh representation of the patient's brain;

selecting a target 3D mesh brain region from the patient-specific 3D mesh representation of the patient's brain;

defining a local coordinate system for the target 3D mesh brain region by performing principal component analysis (PCA) on mesh vertices of the target 3D mesh brain region;

defining 3D mesh sub-regions for the target 3D mesh brain region utilizing the local coordinate system such that at least one of:

the 3D mesh sub-regions have substantially equal length along a long axis of the target 3D mesh brain region, or the 3D mesh sub-regions have substantially equal volume;

defining one or more target points within the target 3D mesh brain region using the local coordinate system;

determining a trajectory for the one or more target points;

determining one or more entry points for the trajectory;

generating a graphical representation of the trajectory and the one or more entry points; and displaying, on a graphical user interface (GUI), the graphical representation of the trajectory and the one or more entry points.

* * * * *